(12) United States Patent
Brion et al.

(10) Patent No.: US 6,258,947 B1
(45) Date of Patent: Jul. 10, 2001

(54) (3,4,7,8,9,10-HEXAHYDRO-6,10-DIOXO-6H PYRIDAZINO[1,2-A] [1,2] DIAZEPINE-1-CARBOXYLIC ACID DERIVATIVES

(75) Inventors: Francis Brion, Toulouse; Veronique Croco, Dijon; Patrick Roussel, Thiais, all of (FR)

(73) Assignee: Aventis Pharma S.A. (FR)

( * ) Notice: Subject to any disclaimer, the term of this patent is extended or adjusted under 35 U.S.C. 154(b) by 0 days.

(21) Appl. No.: 09/296,325

(22) Filed: Apr. 22, 1999

(30) Foreign Application Priority Data

Apr. 27, 1998 (FR) .................................................. 98 05242

(51) Int. Cl.[7] .................................................. C07D 487/04
(52) U.S. Cl. ............................................................ 540/500
(58) Field of Search ............................................. 540/500

(56) References Cited

U.S. PATENT DOCUMENTS

| 4,512,924 | 4/1985 | Attwood et al. | 260/243.3 |
| 5,723,602 | 3/1998 | Karanewsky et al. | 540/500 |

FOREIGN PATENT DOCUMENTS

| 0570764 | 11/1993 | (EP) . |
| 9722619 | 6/1997 | (WO) . |

OTHER PUBLICATIONS

CAS printout of Abstrat and structures of WO 97/22619, Oct. 1997.*

* cited by examiner

Primary Examiner—Bruck Kifle
(74) Attorney, Agent, or Firm—Bierman, Muserlian and Lucas

(57) ABSTRACT

A compound of the formula

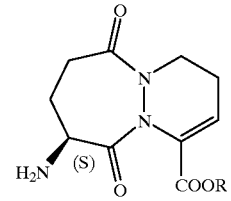

wherein R is alkyl or aralkyl of up to 18 carbon atoms, the amine function being optionally protected are used to prepare compounds of the formula

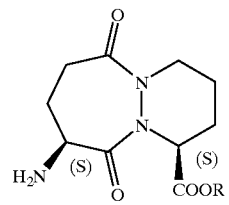

in which R retains its previous meaning and the amine is optionally protected.

11 Claims, No Drawings

(3,4,7,8,9,10-HEXAHYDRO-6,10-DIOXO-6H PYRIDAZINO[1,2-A] [1,2] DIAZEPINE-1-CARBOXYLIC ACID DERIVATIVES

OBJECTS OF THE INVENTION

It is an object of the invention to provide the novel compounds of formula I and a process and intermediates for their preparation.

It is another object of the invention to provide the novel compounds of formula III and a process for their preparation.

These and other objects and advantages of the invention will become obvious from the following detailed description.

THE INVENTION

The novel compounds of the invention are compounds of the formula

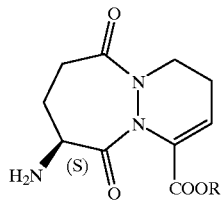
I wherein R is selected from the group consisting of hydrogen, alkyl of 1 to 18 carbon atoms and aryl and aralkyl of up to 18 carbon atoms and the amine is optionally protected.

Examples of R as alkyl are methyl, ethyl, propyl, isopropyl, n-butyl$_1$, isobutyl and tert-butyl and as aryl or aralkyl are benzyl and naphthyl.

Preferred compounds of the invention have the formula

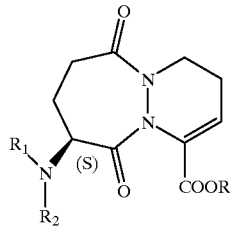
IA wherein A is defined as above, $R_2$ is hydrogen and $R_1$ is selected from the group consisting of

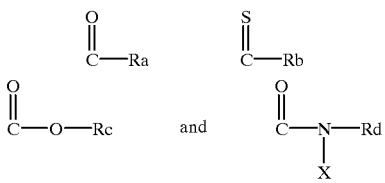

$R_a$, $R_b$, $R_c$ and $R_d$ are individually selected from the group consisting of alkyl of 1 to 18 carbon atoms, aryl and aryl of up to 14 carbon atoms and mono- or polycyclic containing at least one heteroatom and X is selected from the group consisting of hydrogen, alkyl of 1 to 8 carbon atoms and aryl of up to 14 carbon atoms or $R_1$ and $R_2$ together with the nitrogen to which they are attached form a mono- or polycyclic with at least one heteroatom.

Examples of cyclic protective groups are

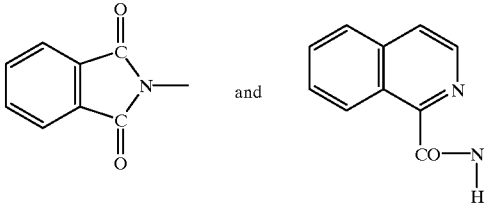

A preferred compound of formula I has the formula

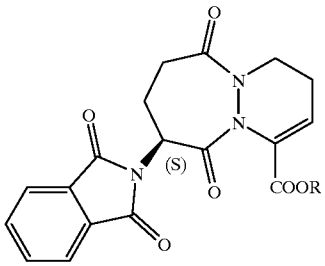
IA$_1$ wherein R is alkyl of 1 to 8 carbon atoms, especially 1,1-dimethylethyl.

The process of the invention for the preparation of a compound of formula I comprises reacting a compound of the formula

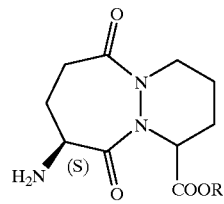
II in racemic form at the 6-member ring and R is as defined and above the amine is protected with a dehydrogenation agent to form the corresponding compound of formula I.

Preferably, the starting material has the formula

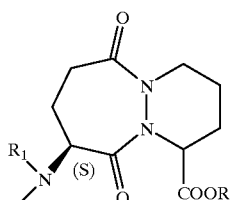
IIA

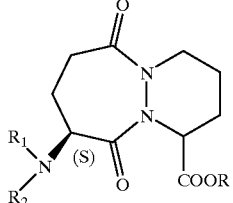

wherein R, $R_1$ and $R_2$ have the above definitions and the dehydrogenation agent is a strong base, an oxidizing agent or a sulfur or selenium derivative.

The compounds of formula II are racemic (SR+SS) at the level of the 6-member ring and are novel products. They can be prepared by the following process.

Préparation a

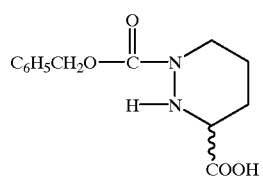

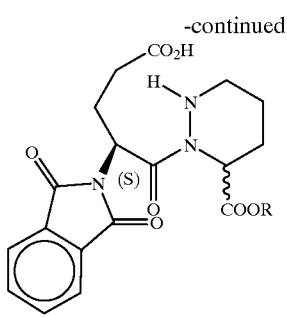

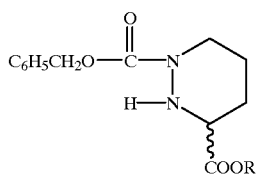

Préparation b

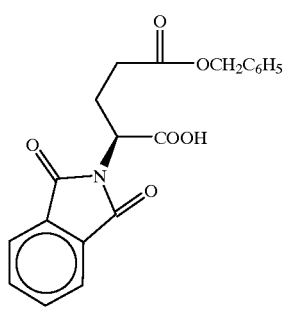

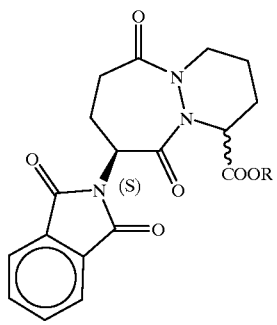

Product of Preparation a
+
Product of Preparation b

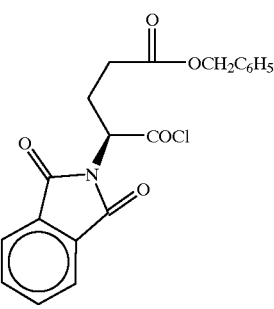

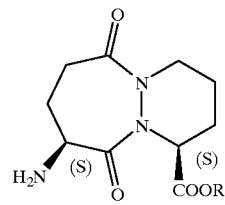

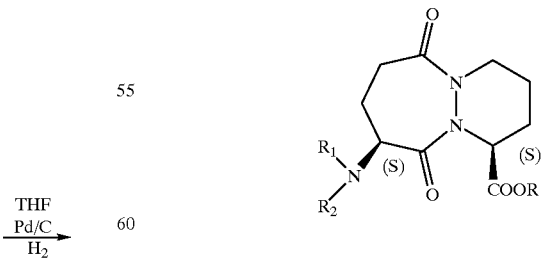

Starting product of Example 1

The starting compounds of the said process are described in or can be prepared as set forth in J. Chem. Soc. Perkins Trans. 1 (1979), Vol. 6, p. 1451–1454 or J. Chem. Soc. Chem. Comm. (1977), p. 635–36.

The process of the invention for the preparation of a compound of the formula

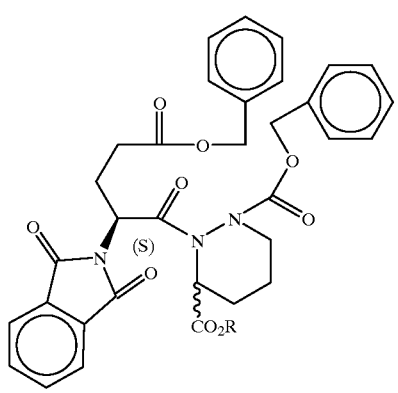

III wherein R is defined as above and the amine is optionally protected comprises reacting a compound of formula I with a reducing agent.

Preferably, the resulting compound has the formula

IIIA wherein R, $R_1$ and $R_2$ are defined as above and the reducing agent is hydrogen in the presence of Raney nickel, palladium on carbon, palladium dihydroxide in the presence of talc, ruthenium on carbon or rhodium in the presence of aluminum, more preferably hydrogen in the presence of Raney nickel. The reaction is effected in the presence of a solvent such as acetic acid, methanol, ethanol, isopropanol, dimethoxyethane, butanone, DMF or acetonitrile.

The compounds of formula IIIA are intermediates for the preparation of pharmacological products such as the compounds described in EP Patent No. 84,095 and in J. Chem. Soc. Perkin Trans. 1, (1986), p. 1011. Other products of formula II are useful in a similar process.

The products of formula II and IIA in the SR form or the form of a mixture (SR+SS) are novel intermediates as are the compounds of formula III and IIIA with the proviso that R is not hydrogen or tert.-butyl in formula III and in formula IIIA, R is not hydrogen or tert.-butyl when the amine is protected by phthalimido. EP 94,095 describes a compound of formula IIIA when R is tert.-butyl and the amine is phthalimido.

In the following examples, there are described several preferred embodiments to illustrate the invention. However, it is to be understood that the invention is not intended to be limited to the specific embodiments.

PREPARATION 1

1,1-dimethyl-ethyl 9-(1,3-dihydro-1,3-dioxo-2H-isoindol-2-yl)-octahydro-6,10-dioxo-6H-pyridazino [1,2-a] [1,2-diazepine-1-carboxylate Preparation a: 1-(benzyl) and 3-(1,1-dimethyl-ethyl) hexahydro-3-(2H)-pyridazinedicarboxylate J. Chem. Soc. Chem. Comm. (1977) p. 635–636 or J. Chem. Soc. Perkin Trans. (1979) Vol 6. p. 1451–1454.

920 µl of $BF_3$-$Et_2O$ and a solution of 18.85 g of terbutyl trichloroacetimidate, 45.5 ml of cyclohexane and 57.5 ml of dichloro methane were introduced at 20° C. into a suspension of 11.50 g of 1,2-benzyl hexahydro-1,3(2H) pyridazinedicarboxylate and 115 ml of dichloromethane. After isolation and purification treatment, the expected product was obtained.

Preparation b: benzyl γ-(chlorocarbonyl)-1,3-dioxo-1 H-isoindole-2(3H)-butanoate 30 g of benzyl γ-carboxy-1,3-dioxo-1H-isoindol-(3H)-butanoate (EP 94,095) were introduced, under a nitrogen atmosphere, into 81 ml of terbutylmethylether. The reaction mixture was then cooled to 0°–2° C. and 17 g of phosphorus pentachloride were added. The reaction mixture was allowed to return to ambient temperature and was stirred for 6 hours, concentrated under reduced pressure, taken to 41° C. and the dry extract obtained was entrained using toluene. The product was held at ambient temperature and under a nitrogen atmosphere, then diluted for use in $CH_2Cl_2$, to obtain a 0.5 M solution of the desired product.

Stage A: 1-(benzyl) 3-(1,1-dimethylethyl)-2-f1,5-dioxo-2-(1,3-dioxo-14-isoindol-2(3H)-yl-5-benzyloxy-pentyll-tetrahydro-1,3-(2H)-pyridazine dicarboxylate A 0.5 M solution of 52 ml of the product of Preparation b in, methylene chloride was cooled to 0°–1° C. and 5.6 g of the product of Preparation a and 22 ml of dichloromethane were added thereto. The reaction mixture was stirred for 3 hours at 0°–1° C. and 1.77 ml of pyridine and 11 ml of methylene chloride were added. The dichloromethane was evaporated under reduced pressure at 30° C., followed by taking up in ethyl acetate, washing with aqueous solutions of sodium chloride and sodium bicarbonate. Extraction was carried out with ethyl acetate, followed by drying, rinsing and extracting under reduced pressure to obtain the desired product which was chromatographed on silica and eluting with a heptane-ethyl acetate mixture 60–40 to obtain 4.697 g of the desired product melting at ≦35° C.

Sage B: γ-[[3-[1,1-dimethylethoxy)carbonyl]-tetrahydro-2(1 H)-pyridazinyl]carbonyl]-1,3-dioxo-1H-isoindole-2-(3H)-butanoic acid A mixture of 4.61 g of the product of Stage A and 47 ml of tetrahydrofuran was mixed at 20° C. and the reaction mixture was hydrogenated at ambient temperature, using 400 mg of palladium on carbon as a catalyst. When the reaction was completed, the reaction mixture was filtered and rinsed with THF to obtain 2.76 g of the desired product.

Stage C: 1,1-dimethylethyl 9-(1,3-dihydro-1,3-dioxo-2H-isoindol-2-yl)-octahydro-6,10-dioxo-6H-pyridazino [1,2-a]-1,2-diazepine-1-carboxylate A solution of 0.846 ml of thionyl chloride in 2.6-ml of dichloromethane was added at 0°+2° C. to a mixture of 2.6 g of the, product of Stage B, 26 ml of methylene chloride and 50 µl of dimethylformamide. The reaction mixture was allowed to return to ambient temperature and was stirred for 6 hours 20 minutes. The isolation and purification operations are carried out to obtain the desired product.

EXAMPLE 1

1,1-dimethylethyl (9S),9-(1,3-dihydro-1,3-dioxo-pyridazino [1,2-a]-diazepine-1-carboxylate a) Preparation of LDA 7.2 ml of butyllithium were added at about −60° over 10 minutes, under a nitrogen atmosphere with stirring to a mixture of 20 ml of THF and 3.2 ml of diisopropylamine. The temperature was allowed to rise to 0° C., was held for 1 hour at 0° C. and then was returned to −600° C.

b) Preparation of $C_6H_5SeBr$ 0.26 of bromine were added at 10° C. to a solution of 1.88 g of diphenyldiselenium and 6 ml of THF. The reaction mixture was stirred for 1 hour at 20° C.

c) Reaction

A mixture of 3.44 g of 1,2-dimethylethyl (1S-cis) 9-(1,3-dihydro-1,3-dioxo-2H-isoindol-2-yl)-octahydro-6,10-dioxo-6H-pyridazino [1,2-a]-1,2-diazepine-1-carboxylate was cooled at −65° C. and the solution of LDA prepared above was added. The reaction mixture was stirred for 10 minutes and the solution of $C_6H_5SeBr$ was added at a temperature of 60° C. +5° C. The temperature was allowed to return to about 0° C. and 4 ml of water, 1.2 of ml of acetic acid and 4 ml of hydrogen peroxide were added. The temperature was allowed to rise to 10° C. and the reaction mixture was stirred for 1 hour. Then, 40 ml of a 10% aqueous solution of sodium chloride and 80 ml of ethyl acetate were added. The reaction mixture was decanted, washed with a saturated solution of sodium chloride, and/or sodium bicarbonate at 10%, followed by evaporation under reduced pressure. The resultant mixture was chromatographed on silica, eluting with a methylene chloride-isopropyl ether mixture to obtain 1.3 g of the desired product with a specific rotation of $α_D$=+126.5° C. =0.335/MeOH Use: 1,1-dimethylethyl (1S-cis) 9-(1,3-dihydro-1,3-dioxo-2H-isoindol-2-yl)-octahydro-6,10-dioxo-6H-pyridazino [1,2-a] [1,2-diazepine-1-carboxylate.

a) Preparation of the catalyst

A mixture of 0.106 g of Raney nickel (Jansen) and 2 ml of sodium hydroxide was stirred for 2 hours at 60° C. and the nickel was washed with water. One drop of acetic acid was added to the last wash water and the nickel was then washed with ethanol and ethyl acetate. The nickel obtained was kept under reduced pressure.

b) Reduction 3 ml of ethyl acetate were added to 0.053 g of nickel prepared as previously and 0.0485 g of the product of Example 1 was added to the suspension obtained. The hydrogenation stage took place at ambient temperature, until there was no further absorption of hydrogen. 2 ml of hydrogen were absorbed and the product had a TLC rf=0.27 eluant isopropyl ether/methylene chloride (50–50).

Various modifications of the products and processes of the invention may be made without departing from the spirit or scope thereof and it is to be understood that the invention is intended to be limited only as defined in the appended claims.

What we claim is:

1. A compound of the formula

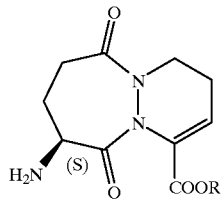

I wherein R is selected from the group consisting of hydrogen, alkyl of 1 to 18 carbon atoms and aryl and aralkyl of up to 18 carbon atoms and the amine is free or protected.

2. A compound of claim 1 of the formula

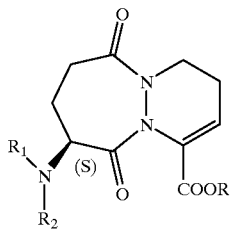

IA wherein R is defined as in claim 1, $R_2$ is hydrogen and $R_1$ is selected from the group consisting of

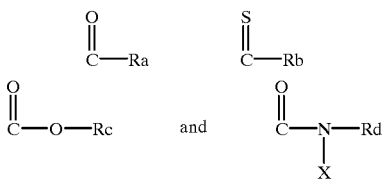

$R_a$, $R_b$, $R_c$ and $R_d$ are individually selected from the group consisting of alkyl of 1 to 18 carbon atoms, aryl of up to 18 carbon atoms and mono- or polycyclic containing at least one heteroatom and X is selected from the group consisting of hydrogen, alkyl of 1 to 8 carbon atoms and aryl of up to 14 carbon atoms or $R_1$ and $R_2$ together with the nitrogen to which they are attached form a mono- or polycyclic with at least one heteroatom.

3. A compound of claim 2 wherein $R_1$ and $R_2$ together with the nitrogen to which they are attached form a polycyclic containing at least one heteroatom.

4. A compound of claim 3 of the formula

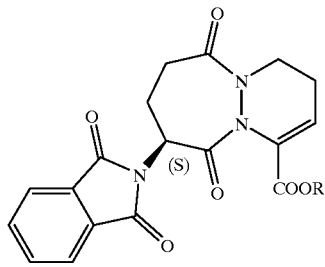

$IA_1$ wherein R is alkyl of 1 to 8 carbon atoms.

5. A compound of claim 1 wherein R is 1,1-dimethylethyl.

6. A compound of claim 1 which is 1,1-dimethylethyl (9S), 9-(1,3-dihydro-1,3-dioxo-2H-isoindol-2-yl)-3,4,7,8,9,10-hexahydro-6,10-dioxo-6H-pyridazino [1,2-a]-diazepine-1-carboxylate.

7. A process for the preparation of a compound of claim 1 wherein R has the definition of claim 1 and the amine is protected comprising reacting a compound of the formula

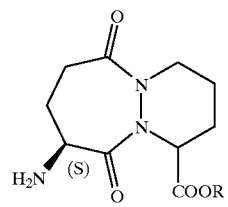

II wherein R has the definition of claim 1 and the amine is protected with a dehydrogenation agent.

8. The process of claim 7 wherein the starting compound has the formula

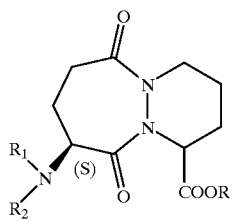

IIA wherein R is defined, as in claim 1, $R_2$ is hydrogen and $R_1$ is selected from the group consisting of

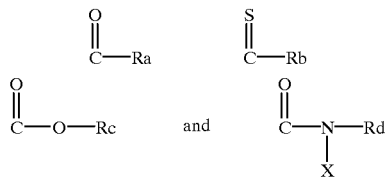

$R_a$, $R_b$, $R_c$ and $R_d$ are individually selected from the group consisting of alkyl of 1 to 18 carbon atoms, aryl of up to 18 carbon atoms and mono- or polycyclic containing at least one heteroatom and X is selected from the group consisting of hydrogen, alkyl of 1 to 8 carbon atoms and aryl of up to 14 carbon atoms or $R_1$ and $R_2$ together with the nitrogen to which they are attached form a mono- or polycyclic with at least one heteroatom.

9. A process for the preparation of a compound of the formula

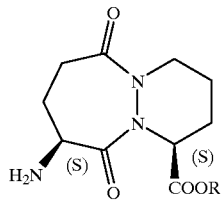

III wherein R is selected from the group consisting of hydrogen, alkyl of 1 to 18 carbon atoms and aryl and aralkyl of up to 18 carbon atoms and the amine is optionally protected comprising reacting a compound of claim 1 with a reducing agent.

10. The process of claim 9 wherein the reducing agent is hydrogen in the presence of Raney nickel.

11. A process for the preparation of a compound of the formula

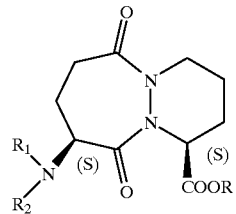

IIIA wherein R is selected from the group consisting of hydrogen, alkyl of 1 to 18 carbon atoms and aryl and aralkyl of up to 18 carbon atoms, $R_2$ is hydrogen and $R_1$ is selected from the group consisting of

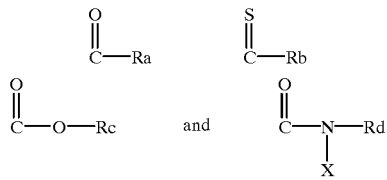

$R_a$, $R_b$, $R_c$ and $R_d$ are individually selected from the group consisting of alkyl of 1 to 18 carbon atoms, aryl of up to 18 carbon atoms and mono- or polycyclic containing at least one heteroatom and X is selected from the group consisting of hydrogen, alkyl of 1 to 8 carbon atoms and aryl of up to 14 carbon atoms or $R_1$ and $R_2$ together with the nitrogen to which they are attached form a mono- or polycyclic with at least one heteroatom comprising reacting a compound of claim 2 with a reducing agent.

* * * * *